United States Patent
Geret et al.

(10) Patent No.: US 9,554,994 B2
(45) Date of Patent: Jan. 31, 2017

(54) COMPOSITION IN FORM OF A GEL FOR THE VIRUCIDAL DISINFECTION OF MAMMALIAN SKIN

(75) Inventors: Laurence Geret, Pulheim (DE); Bernhard Meyer, Mettmann (DE); Stefan Jäger, Köln (DE)

(73) Assignee: Ecolab USA Inc., St. Paul, MN (US)

( * ) Notice: Subject to any disclaimer, the term of this patent is extended or adjusted under 35 U.S.C. 154(b) by 493 days.

(21) Appl. No.: 13/515,639

(22) PCT Filed: Dec. 16, 2009

(86) PCT No.: PCT/EP2009/067241
§ 371 (c)(1),
(2), (4) Date: Jul. 18, 2012

(87) PCT Pub. No.: WO2011/072728
PCT Pub. Date: Jun. 23, 2011

(65) Prior Publication Data
US 2013/0197098 A1    Aug. 1, 2013

(51) Int. Cl.
| | | |
|---|---|---|
| *A61K 9/00* | (2006.01) | |
| *A01N 25/04* | (2006.01) | |
| *A61K 8/04* | (2006.01) | |
| *A61K 8/34* | (2006.01) | |
| *A61K 31/045* | (2006.01) | |
| *A61Q 17/00* | (2006.01) | |

(52) U.S. Cl.
CPC ............. *A61K 9/0087* (2013.01); *A01N 25/04* (2013.01); *A61K 8/042* (2013.01); *A61K 8/34* (2013.01); *A61K 31/045* (2013.01); *A61Q 17/005* (2013.01)

(58) Field of Classification Search
CPC ................................ A61K 9/00; A61K 9/0087

USPC .......................................................... 514/724
See application file for complete search history.

(56) References Cited

U.S. PATENT DOCUMENTS

| | | | |
|---|---|---|---|
| 4,976,953 A | 12/1990 | Orr et al. | |
| 5,043,357 A | 8/1991 | Höffler et al. | |
| 5,376,366 A * | 12/1994 | Petchul ................. | A61K 8/042 424/78.03 |
| 5,981,605 A * | 11/1999 | Thomsen et al. ............. | 514/724 |
| 7,470,656 B2 | 12/2008 | Sherry et al. | |
| 2003/0104040 A1 | 6/2003 | Kirby et al. | |
| 2003/0235550 A1 | 12/2003 | Pan et al. | |
| 2005/0106122 A1 | 5/2005 | Gizurarson et al. | |
| 2007/0274926 A1 | 11/2007 | Fuls et al. | |
| 2008/0138438 A1 | 6/2008 | Taylor et al. | |
| 2009/0018213 A1 | 1/2009 | Snyder et al. | |

FOREIGN PATENT DOCUMENTS

| | | |
|---|---|---|
| DE | 19502456 C | 9/1996 |
| EP | 0465423 | 1/1992 |
| EP | 2272339 | 1/2011 |
| WO | WO 95/13790 | 5/1995 |
| WO | WO 02/069887 | 9/2002 |

OTHER PUBLICATIONS

Poli et al., Food Chemistry, 1979;4(3):251-258.*

* cited by examiner

*Primary Examiner* — San-Ming Hui
(74) *Attorney, Agent, or Firm* — Merchant & Gould P.C.

(57) ABSTRACT

The present invention describes a composition in form of a gel for the virucidal disinfection of mammalian skin comprising 71 to 95 weight percent of a C1 to C3 monoalcohol, 0.01 to 1 weight percent thickener and wherein the composition has a viscosity range of from 3000 to 19000 mPas measured at 20° C. with spindle LV3 at a speed of 2.5 rpm. Furthermore, the invention describes a method for virucidal disinfection of skin.

12 Claims, No Drawings

COMPOSITION IN FORM OF A GEL FOR THE VIRUCIDAL DISINFECTION OF MAMMALIAN SKIN

The present invention relates to a composition in form of a gel for the virucidal disinfection of mammalian skin. More specifically the invention relates to a virucidal composition in form of a gel meeting the requirements of the European standard EN 14476 (2005).

Skin disinfectants especially for disinfecting hands are used in several fields where a contamination and especially a cross contamination with bacteria and viruses should be avoided. One difficult field is the inactivation of viruses on the skin because different viruses have a different sensitivity to the different disinfectants. This means whilst one type of virus is sufficiently inactivated by the disinfectant, a different virus is inadequately inactivated. However, a disinfectant applied for virucidal disinfection should be able to inactivate all possible viruses which are present on the skin particularly on the hands and nails.

Two classes of viruses exist: The enveloped viruses are surrounded by a lipid envelope and are normally inactivated by compounds destroying this lipid envelope. These viruses are lipophilic, examples are Herpes simplex virus, Influenza virus, Vakzinia virus, HIV, Hepatitis-B. The inactivation of enveloped viruses is easy.

Also non-enveloped so called naked viruses exist which do not have a lipoid envelope. These viruses are hydrophilic, examples are Poliovirus, Adenovirus, Hepatitis A virus, and Simian virus 40. Naked viruses are much more stable against conventional virucidal disinfectants.

For the classification of virucidal disinfectants the European standard EN14476 (March 2005) exists in which the test methods, the test viruses, and the conditions for measuring the inactivation of specific test viruses are described. According to this standard hand disinfectants are classified as virucidal if they can inactivate certain viruses within a certain time and to a specific extent. The European standard EN14476 uses as test viruses for virucidal compositions for hand disinfection Poliovirus (type 1, strain LSc-2ab) and Adenovirus (type 5, strain Adenoid 75, ATCCVR-5). The standard also describes the test procedure and the way of measuring the inactivation of the test viruses. A virucidal disinfectant according to the European standard EN14476 of April 2005 inactivates the test viruses Poliovirus and Adenovirus within a given contact time by 4 $\log_{10}$ units, which means the inactivation of the virus is 99.99%.

If a virucidal composition is used for skin especially for hand disinfection it is important that the composition not only inactivates the viruses but also is skin-compatible because the virucidal composition is frequently used. In hospitals, for example, virucidal hand disinfection is under specific circumstances carried out after each treatment of a patient. That means that a nurse or a doctor working in a hospital uses the virucidal hand disinfectant twenty to forty times a day. Several virucidal disinfectants of the state of the art do not fulfill the criteria of being skin-compatible even if frequently used. These virucidal disinfectants contain, for example, high amounts of acids so that the compositions have a pH value lower than 3 which will damage the skin especially if the composition is frequently used. Other virucidal compositions have a higher pH, but contain virucidal enhancers which also irritate the skin or are hazardous substances.

It is important that a virucidal composition for skin and especially hand disinfection therefore does not only fulfill the criteria to inactive the most resistant viruses but also has to be skin-compatible even if frequently used. These two conditions are quite difficult to meet as at least for naked viruses the inactivation is higher at a lower pH. On the other side the lower the pH is, the more aggressive is the composition to the skin.

The further disadvantage is that if virucidal compositions are used containing ingredients with a low boiling point like ethanol which evaporate fast the necessary concentration of the component decreases during the contact time and reaches after some time during the treatment a level which is not high enough to inactivate the viruses sufficiently. For example, if ethanol in a high concentration is used as virucidal agent for contact times of two minutes or more the concentration of the ethanol constantly decreases so that after one minute contact time the concentration of the ethanol is between one forth and one third lower than at the beginning of the treatment.

For example, if ethanol in a high concentration is used as virucidal agent for contact times of two minutes or more the product evaporates from the skin rapidly. As a consequence the user should apply after one minute again an additional dosage of the virucidal composition so that the amount of product is sufficient during the complete contact time in which the disinfectant is used. This disadvantage can be avoided if the virucidal composition is thickened in form of a gel to reduce the evaporation during use and allow a more constant application of the virucidal composition on the skin.

Also liquids are spilled in the environment during application. This spillage is significantly reduced, when products are applied in the form of a gel.

The present invention relates to a new virucidal composition in form of a gel for the virucidal disinfection of mammalian skin which fulfils the requirements of the European standard EN14476 and allows an inactivation of the test viruses within two minutes or less by at least 4 $\log_{10}$ units.

From the state of the art gel-like compositions comprising alcohols especially ethanol are already known and were used for disinfection. However, these compositions were only used for disinfection against bacteria not against viruses because the gel compositions of the state of the art do not fulfill the requirements of the European Standard EN 14476.

In hospitals for examples these gels were not broadly used in the past because their antimicrobial activity is known to be much lower than of the non-thickened ethanol, which are known to be virucidal disinfectants but which have the above mentioned disadvantage of a fast evaporation from the skin.

Furthermore, from the state of the art it is known that, for example, in the case of alcohol the fluid non-thickened alcohol has a higher virucidal activity compared to gel comprising the same concentration of alcohol.

EP 1 281 319 A1 describes an alcoholic gel comprising a high concentration of ethanol, a thickener, a skin-care agent and an amine oxide. The gel is used for disinfection of hands. The document does not comprise any information about the virucidal effect of such a composition. Furthermore, the thickening system which is used for the alcoholic gel comprises amine oxides as co-thickener which might irritate the skin.

WO 2008/059885 A1 describes a gel-like disinfecting composition. The composition comprises ethanol and/or isopropanol in a concentration of 40 to 95 weight percent and a thickener which is a carboxyvinyl polymer and low-strength agar. The document does not describe that the gel-like composition is used as a virucidal disinfectant. The document also does not contain any specific information about the viscosity of the gel.

WO 2007/095008 A2 describes an antiviral composition which is used for the inactivation of non-enveloped viruses. The composition comprises ethanol in high concentration and a polyquaternium compound or copper gluconate as a virucidal enhancer. Table 12 shows that a composition comprising 70 percent ethanol, 0.4 percent polyquaternium-37 and 0.08 percent copper gluconate inactivates adenovirus and poliovirus within one minute by at least 4 $\log_{10}$ units. However, the document does not describe the use of a composition as a gel.

WO 2008/049454 A1 describes a virucidal composition comprising 80 to 99 weight percent of a monoalcohol and a mixture of an organic acid and an alkoxylated monoglyceride and/or alkoxylated diglyceride. The composition is used for inactivating viruses especially poliovirus, adenovirus and SV40 virus. However, the document does not describe the use of the virucidal composition in form of a gel and contains virucidal enhancers.

The disadvantage of the alcohol-based hand gels in the state of the art is that their virucidal efficiency is significantly lower than for alcohol-based compositions in fluid form. Therefore, in most hospitals still liquid hand rubs are used and the use of hand gels has not become popular because their virucidal activity is significantly lower than of alcohol-based hand rubs. As a consequence the healthcare workers have been advised not to use gels.

The use of the gel has the advantage that a gel better adheres to the skin and the alcohol does not evaporate so fast during use of the hand disinfectant. For example, if ethanol is used in high concentration and fluid form as hand disinfections it is necessary to dose ethanol additionally after a contact time of one minute to avoid a decrease in the ethanol concentration because of evaporation from the skin during use under a virucidal active concentration. When using gels this can be avoided. Also spillage of product during application is avoided, when using a gel.

However, until now the state of the art does not provide the composition in form of a gel for the virucidal disinfection of mammalian skin fulfilling the requirements of the European standard EN14476 (2005) for virucidal hand disinfection.

It was the technical object of the present invention to provide a composition in form of a gel for the virucidal disinfection of mammalian skin having a higher virucidal activity and fulfilling the European standard EN14476 (2005).

The technical object is solved by a composition in form of a gel for the virucidal disinfection of mammalian skin comprising 71 to 95 weight percent, preferably 85 to 95 weight percent of a C1 to C3 monoalcohol, 0.01 to 1 weight percent of thickener, preferably 0.01 to 0.5 weight percent, most preferably 0.1 to 0.4 weight percent of thickener. The composition has a viscosity range of from 3000 to 19000 mPas, preferably 3000 to 16500 mPas, most preferably 5000 to 9000 mPas all measured at 20° C. with spindle LV3 at a speed of 2.5 rpm. The viscosity was measured with a Brookfield Digital Viscometer LVDV-II+ according to DIN 53019. The viscosities were measured in mPas.

In a preferred embodiment the composition according to the invention does not comprise any virucidal enhancers like, for example, percarboxylic acids, inorganic acids, aldehydes, organic C1 to C10 acids and aminoxides. The virucidal composition in form of a gel is used for the disinfection of mammalian skin, preferably skin of a human being and most preferably for the hands of a human being.

In a further preferred embodiment the composition in form of a gel is used for the inactivation of non-enveloped viruses, preferably for the inactivation of poliovirus (type 1, strain LSc-2ab) and adenovirus (type 5, strain Adenoid 75).

The term "virucidal disinfection" as used in the claims and throughout the description means an inactivation of the test viruses poliovirus and adenovirus by at least 4 $\log_{10}$ units in at most two minutes contact time under the conditions and methods according to the European standard EN14476 (2005).

The standard describes the test viruses which are used for the examination of virucidal compositions, the test methods and the necessary grade of inactivation of the test viruses. The standard prescribes that a product has to be tested according to part 6 and 7 of the European standard EN14476 and that the reduction of a concentration of viruses of the test viruses has to be at least 4 $\log_{10}$ units if it is tested under the conditions described in table 1 under part 4 of the standard. Table 1 of part 4 of the standard describes the test conditions for a virucidal composition for hand disinfection. The test virus is poliovirus and adenovirus. As poliovirus (type 1, strain LSc-2ab) as used and as adenovirus (type 5, strain Adenoid 75). The test viruses are described in table 2 of part 5.3.1 of the European standard EN 14476. Both test viruses are non-enveloped viruses. The test condition is 20° C. plus minus 1° C. and the contact time is one minute or thirty seconds as obligatory contact time and three minutes as additional contact time.

The term "mammalian skin" as used in the claims and throughout the specification means skin of a mammal like human being or animal.

The inventors have found that if a gel composition according to the invention is used only consisting of a monoalcohol and a thickener within a certain viscosity range of 3000 to 19000 mPas the sufficient inactivation of both viruses poliovirus and adenovirus was obtained by at least 4 $\log_{10}$ units in at most two minutes contact time.

In a preferred embodiment the C1 to C3 monoalcohol is selected from the group consisting of methanol, ethanol and, 2-propanol or mixtures thereof. The most preferred monoalcohol is ethanol which can contain up to 30 weight percent of other C1 to C3 monoalcohols.

The composition furthermore comprises a thickener. The concentration of the thickener is 0.01 to 1 weight percent, preferably 0.1 to 0.4 weight percent. As the thickener preferably a thickener selected from the group consisting of a polyacrylic acid, a polyacrylate, a copolymer of a polyacrylic acid and a polyacrylic acid alkyl ester, a copolymer of a polyacrylate and a polyacrylic acid alkyl ester is used.

Furthermore, other auxiliary thickeners can be used in the composition. Examples of those thickeners include cellulose, cellulose derivatives such as hydroxyethyl cellulose, hydroxypropyl cellulose, hydroxypropylmethyl cellulose, hydrophobized hydroxypropylmethyl cellulose, methyl cellulose, carboxymethyl cellulose sodium, copolymers having acrylic acid or a salt thereof as a constituent, such as cross-linked acrylic acid-starch graft copolymer and N-vinylacetamide/sodium acrylate copolymer, polyvinyl alcohol, polyvinyl pyrrolidone, polyethylene oxide, methyl vinyl ether/maleic anhydride copolymer, polyacrylamide, alginic acid, sodium alginate, propylene glycol alginate, gelatin, gum arabic, gum-tragacanth, locust bean gum, guar gum, tamarind gum, xanthan gum, gellant gum, carrageenan. These thickeners may be used alone or in combination.

If thickeners are used consisting of polyacrylic acids or copolymers of polyacrylic acid it is necessary to additionally include a neutralizer in the composition. This neutralizer may be any agent which is suitable for use on external skin and which can increase the pH of the composition. Examples of such neutralizers generally include organic amines like, for example, alkanolamines such as monoethanolamine, diethanolamine, triethanolamine, monoisopropanolamine, diisopropanolamine and triisopropanolamine, alkylamines such as 2-amino-2-methyl-1-propanol, 2-amino-2-methyl-1,3 propanediol, N-tetrahydroxypropylethylendiamine.

In a preferred embodiment the composition according to the invention has a pH of 5 to 8.5 preferably 6 to 8 if measured at 20° C.

The usual virucidal composition quite often contains high amounts of acids which are used as a virucidal enhancer. As a consequence the compositions often have a pH value below 5 and even below 3. Such concentration of high acidity damages the skin especially if the composition for the inactivation of viruses is more frequently used. An additional advantage of the present invention is that such enhancers are not used in the composition according to the invention and that the pH is skin friendly. As a consequence the skin is not irritated even if the composition is used frequently.

In a preferred embodiment the composition can furthermore comprise additives selected from the group consisting of stabilizers, fragrances, colorants and emulsifiers, wetting agents or mixtures thereof.

In a preferred embodiment the composition also comprises skin care agents like, for example, moisturizing agents or emollients (re-greasing substances).

A further disadvantage of alcoholic gels of a state of the art is that these gels quite often clog dispenser and dispenser pumps during application of the gel. The composition according to the invention has due to its viscosity range and its composition the additional advantage that such clogging of dispensers is avoided.

A composition in form of a gel according to the invention is prepared by adding the thickener to water and thoroughly stirring the mixture to obtain a homogenous solution. After that the necessary amount of monoalcohol is added and the solution is further stirred until being homogenous. Subsequently additives like skin care ingredients and emollients can be added. To reach the final viscosity the neutralizer dissolved in the remaining amount of monoalcohol is added and the solution is mixed until the gel is homogenous and the viscosity is in the prescribed range.

The composition in form of a gel for the virucidal disinfection according to the invention has a broad virucidal activity and is particularly skin-compatible because the pH value is in a range of 5 to 8 which is a pH range not affecting the skin. In addition, the composition meets the obligations of the European standard EN 14476 (2005) and achieves an inactivation of the test viruses poliovirus and adenovirus by at least 4 $\log_{10}$ units in at most two minutes contact time according to the test procedure described in EN 14476 (2005).

The virucidal composition according to the invention is used on human or animal skin and it is preferably used for hand disinfection, for example in surgery or nursery. Hand disinfectants are normally used in hospitals, nursing homes and in the surgical field. However, they can be used, too, for the disinfection in food processing plants, for example meat and/or poultry processing plants as well as in the disinfection of beverage processing plants.

With a composition according to the invention contamination or cross contamination even with highly resistant naked viruses like poliovirus can be avoided. Furthermore, it is guaranteed that even after a short period of treatment the virus titer is sufficiently reduced. The virucidal composition furthermore is highly compatible to skin even if used twenty or forty times a day. The composition is preferably applied with the hands following by rubbing and distributing the composition evenly over the skin. The virucidal composition according to the invention can be applied by using a dispenser or solid support soaked with the virucidal composition. Furthermore, as a support a woven or non-woven fabric can be used as textile, paper towel, cotton wool, an absorbent polymer sheet or a sponge.

Contrary to the gel compositions of the state of the art the virucidal composition according to the invention does not leave greasy films on the disinfected skin. Said greasy films have the effect that a firm grip which may be necessary during treatment of patients is no longer ensured. Furthermore the skin feeling also becomes uncomfortable.

The invention further relates to a method for virucidal disinfection of mammalian skin comprising the steps of providing a composition according to the invention and contacting the skin with a composition for at most two minutes to reduce the virus titer at least 4 $\log_{10}$ steps.

In a preferred embodiment the inactivated viruses are selected from the group consisting of poliovirus, adenovirus, vaccinia virus or mixtures thereof.

The following examples further illustrate the invention.

EXAMPLES

Example 1

Preparation of the Composition 0.230 gram of the thickener was added to 6.0445 gram of water and thoroughly mixed to obtain a homogenous dispersion. Then, 86.575 gram of ethanol (96 percent V/V Ph.Eur.grade) was added to the mixture and stirred until homogenous. To the solution 2.9475 gram of skin care ingredients and emollients were added and mixed for further 10 minutes. To reach the final viscosity 0.378 gram of tetrahydroxypropylethylendiamine as neutralizer dissolved in 3.825 gram ethanol (96 percent V/V Ph. Eur. grade) was added and the solution stirred until the system became homogenous. The viscosity of the composition was measured acc DIN 53019 with a Brookfield Digital Viscometer LVDV-II+ at 20° C., spindle LV3, speed 2.5 rpm at 8200 mPas.

In the same way further virucidal compositions according to the invention were prepared. The viscosity of the examples was measured as described above. The inactivation of the test viruses poliovirus and adenovirus was measured according to the procedure described in European standard EN14476 (2005). The following table 1 shows the results.

In table 1 examples 1, 2 and 3 are examples according to the invention all with an ethanol concentration of 85% w/w and with different viscosities. Comparative example 4 is an example having a higher viscosity of 20252 mPas measured as described before. Comparative example 5 is an example only with ethanol without any thickener.

TABLE 1

| Description | Example 1 Quantity in % w/w | Example 2 Quantity in % w/w | Example 3 Quantity in % w/w | Comparative Example 4 Quantity in % w/w | Comparative Example 5 Quantity in % w/w |
| --- | --- | --- | --- | --- | --- |
| Water, deionized | 11.4445 | 11.3285 | 11.4735 | 11.0875 | 12.0525 |
| Thickener system | 0.230 | 0.2740 | 0.2190 | 0.3650 | — |
| Ethanol, denatured | 85.0000 | 85.0000 | 85.0000 | 85.0000 | 85.0000 |
| Skin Care ingredients and Emollients | 2.9475 | 2.9475 | 2.9475 | 2.9475 | 2.9475 |
| Neutralizer (Tetrahydroxypropylethylendiamine) | 0.378 | 0.4500 | 0.3600 | 0.6000 | — |
| pH measured at 20° C. 10% solution in water | 7.6 | 7.6 | 7.5 | 7.5 | 7.6 |
| Brookfield Digital Viscometer LVDV-II + [mPas]; spindle LV3, speed 2.5 rpm, T = 20° C. | 8200 | 9900 | 5900 | 20250 | 0 |
| Reduction of Adeno* acc to EN 14476, contact time 2 min | pass >$\log_{10}$ 4.86 | pass >$\log_{10}$ 4.43 | pass >$\log_{10}$ 5.43 | failed $\log_{10}$ 1.57 | pass >$\log_{10}$ 4.43 |
| Reduction of Polio** acc to EN 14476, contact time 2 min | pass >$\log_{10}$ 4 | pass >$\log_{10}$ 4 | pass >$\log_{10}$ 4 | failed <$\log_{10}$ 1.71 | pass >$\log_{10}$ 4 |
| Virucidal acc to EN 14476, contact time 2 min | pass | pass | pass | failed | pass |

*Adeno virus type 5, strain adenoid 75, ATCC VR-5
**Polio virus type 1, LSc-2ab

From the tables can be seen that the compositions according to the invention which are shown in examples 1, 2, 3 having a viscosity in the range of 5900 to 9900 all show a virus inactivation of at least 4 $\log_{10}$ units after 2 minutes contact time. The pH of the examples was measured in a 10% water solution. It can be seen that the composition according to the invention is neutral which means that it is very skin friendly even if used frequently.

In contrast the comparative example 4 which is an alcoholic gel of the state of the art having a higher viscosity of 20250 mPas showed a virus titer reduction of adenovirus of only 1.57 $\log_{10}$ units and of poliovirus of only 1.71 $\log_{10}$ and therefore failed the virucidal test according to EN 14476 after a contact time of two minutes. Comparative example 5 is an example only comprising ethanol and water with skin care agents without a thickener system. It can be seen that if the viscosity is zero the adenovirus and poliovirus are also inactivated and the virucidal composition passes.

The invention claimed is:

1. Composition in form of a gel for the virucidal disinfection of mammalian skin comprising:
    85 to 95 wt-% of a C1 to C3 monoalcohol,
    0.01 to 0.4 wt-% of thickener comprising an acrylate, wherein the thickener results in the composition having a viscosity in the range from 3000 to 9000 mPas measured at 20° C. with spindle LV3 at a speed of 2.5 rpm, and
    a neutralizer comprising tetrahydroxypropylethylendiamine in an amount that results in a pH of 6 to 8,
    wherein the composition is free of virucidal enhancers selected from percarboxylic acid, inorganic acid, aldehydes, organic C1 to C10 acid, and aminoxides; and wherein the composition is capable of inactivation of one or more non-enveloped viruses by at least 4 $\log_{10}$ within two minutes or less.

2. Composition according to claim 1, wherein the composition is formulated for use for the virucidal disinfection of hands.

3. Composition according to claim 1, wherein the composition is capable of inactivation of poliovirus (type 1, strain LSc-2ab) and adenovirus (type 5, strain Adenoid 75).

4. Composition according to claim 1, wherein the composition is capable of inactivating poliovirus and adenovirus by greater than or equal to 4 $\log_{10}$ units in less than or equal to 2 min contact time.

5. Composition according to claim 1, wherein the C1 to C3 monoalcohol is selected from the group consisting of methanol, ethanol and 2-propanol or mixtures thereof.

6. Composition according to claim 1, wherein the C1 to C3 monoalcohol comprises ethanol, and wherein the composition can contain up to 30 wt-% of other C1 to C3 alcohols.

7. Composition according to claim 1, wherein the concentration of the thickener is 0.1 to 0.4 wt-%.

8. Composition according to claim 1, wherein the viscosity is in a range of from 5000 to 9000 mPas.

9. Composition according to claim 1, wherein the thickener is selected from the group consisting of a polyacrylic acid, a polyacrylate, a copolymer of a polyacrylic acid and a polyacrylic acid alkylester, a copolymer of a polyacrylate and a polyacrylic acid alkyl ester.

10. Composition according to claim 1, wherein the composition has a pH of 5 to 8.

11. Method for virucidal disinfection of mammalian skin comprising:
    contacting the skin with the composition of claim 1 for at most 2 min to inactivate the virus titre for at least 4 $\log_{10}$ units.

12. The composition of claim 1, wherein the thickener comprises polyacrylic acid or copolymer of polyacrylic acid and the composition further comprises an alkanolamine, alkylamine, or combination thereof.

* * * * *